(12) United States Patent
Ahari

(10) Patent No.: US 6,264,685 B1
(45) Date of Patent: Jul. 24, 2001

(54) FLEXIBLE HIGH RADIAL STRENGTH STENT

(75) Inventor: Frederick Ahari, Clearwater, FL (US)

(73) Assignee: Datascope Investment Corp., Montvale, NJ (US)

( * ) Notice: Subject to any disclaimer, the term of this patent is extended or adjusted under 35 U.S.C. 154(b) by 0 days.

(21) Appl. No.: 09/347,747

(22) Filed: Jul. 6, 1999

(51) Int. Cl.[7] ........................................ A61F 2/04
(52) U.S. Cl. .......................................... 623/1.15
(58) Field of Search ..................... 623/1.15, 1; 606/198

(56) References Cited

U.S. PATENT DOCUMENTS

| | | | |
|---|---|---|---|
| 5,449,373 | * 9/1995 | Pinchasik et al. | 606/198 |
| 5,733,303 | * 3/1998 | Israel et al. | 606/198 |
| 5,755,781 | * 5/1998 | Jayaraman | 623/1 |
| 5,824,036 | 10/1998 | Lautherjung | 623/1 |

* cited by examiner

Primary Examiner—Cary E. O'Connor
(74) Attorney, Agent, or Firm—Abraham P. Ronai

(57) ABSTRACT

A flexible high radial strength stent comprising one or more flex cells and primary cells. The primary cells comprising elongated members having first and second ends and extending in a circumferential direction around an axis and curving in two opposite directions transverse to the circumferential direction. The elongated members are joined to one another on their first ends forming cusps. The flex cell may comprise a member in the shape of a U, V, ellipse, rhombus, parallelogram, or other similar shape. The flex cell has two ends, or in the case of the parallelogram two vertices, each of which is attached to the adjacent second end of a neighboring elongated member.

15 Claims, 5 Drawing Sheets

FLEXIBLE HIGH RADIAL STRENGTH STENT

FIELD OF THE INVENTION

The present invention relates generally to prosthetic devices for use within a body passageway or duct and, more particularly, to an intraluminal stent for repairing blood vessels. Still more particularly, the present invention relates to flexible intraluminal stents having high radial strength.

BACKGROUND OF THE INVENTION

As its name implies, intraluminal stents are devices which are implantable within a body lumen for treating abnormal conditions within the lumen. For example, these devices have found use in maintaining the patency of collapsing and partially occluded blood vessels, particularly to prevent acute closure and restenosis after a vessel has been enlarged by a percutaneous transluminal coronary angioplasty procedure. These devices have also been used to reinforce other body lumens, such as the urinary tract, the bile tract, the intestinal tract and the like. They have found further use as fixation devices for holding intraluminal prosthetic grafts open and in place in the repair of weakened or abnormally dilated portions of a blood vessel.

Conventional stents are formed from a wire or the like which has been bent back and forth in a generally zig-zag pattern in a longitudinal direction and then wound in a circumferential direction transverse to the longitudinal direction to form one or more loops of a predetermined circumference. Typically, the stent is radially expandable from a collapsed condition in which the circumference of the stent is minimized so that the stent can be delivered intraluminally, to an expanded condition in which the circumference of the stent approaches the predetermined circumference to support and reinforce the lumen. The stent is normally held in the collapsed condition by a catheter during intraluminal delivery to the repair site. Once properly located, the stent is removed from the catheter and radially expanded until its circumference firmly contacts the interior wall of the lumen to hold the stent in this implanted location. This radial expansion of the stent may be effected by the dilation of an angioplasty balloon placed axially within the stent. Alternatively, the stent may be made from a shape memory metal, whereby the stent will automatically assume its expanded circumference as its temperature increases upon implantation at the desired location.

Regardless of the mechanism by which the stent is placed in its expanded condition, an important attribute of the stent is its ability to provide radial support. This capability is a concern not only where the stent is being used to maintain the patency of the lumen in which it is located, but also where the stent is being used in conjunction with a prosthetic graft to keep the graft open and to hold it at the location at which it was implanted. The ability of the stent to provide this radial support, particularly over long periods of time, is directly related to the hoop or radial strength which the stent exhibits. For conventional stents having a generally zig-zag configuration, the hoop strength depends primarily upon the number of bends along the circumference of the stent, the elastic properties of the wire from which the stent is formed, and the diameter of the wire. Currently available stents generally have a sufficient hoop strength for use in small caliber vessels and the like because they require a relatively small number of bends along their circumference. However, where the stents have a larger circumference for use in larger caliber vessels, such as the aorta, they include a much larger number of bends and thus exhibit a lower hoop strength which is generally insufficient to maintain the patency of these larger lumens and to fix larger circumference grafts in place therein. A simple approach to increasing the hoop strength of these stents without changing the material from which they are formed is to form the stent from a larger diameter wire. Although this approach may produce satisfactory hoop strengths, it has the negative affect of increasing the bulk of the stent and thus contributes to delivery problems.

U.S. Pat. No. 5,630,829, issued to Lauterjung, discloses a stent having sufficient hoop strength to provide long term radial support and graft fixation in large caliber arteries and other body lumens. More particularly, the stent therein disclosed exhibits high hoop strength with little to no increase in bulk over conventional stents and which, therefore, does not contribute to difficulties in intraluminal delivery.

There exists a need however, for a high hoop strength stent, as described above, that is highly flexible, and thus capable of matching the anatomical geometry of the patient.

SUMMARY OF THE INVENTION

Accordingly, the present invention comprises an intraluminal stent, as disclosed in U.S. Pat. No. 5,630,829, said reference being herein incorporated by reference, further including the incorporation of one or more flex cells for enhancing the flexibility of the stent. The stent includes a plurality of elongated members having first and second ends and extending in a circumferential direction around an axis and curving in two opposite directions transverse to the circumferential direction. Each of the elongated members may be curved over substantially its entire extent, preferably so that the curved portions define an arc of a circle. The elongated members are joined to one another on their first ends forming cusps pointing in opposite axial directions. The cusps are movable in opposite axial directions between an expanded condition, in which the opposed cusps are relatively close to one another and the elongated members define an expanded circumference, and a collapsed condition, in which the opposed cusps are relatively distant to one another and the elongated members define a collapsed circumference which is smaller than the expanded circumference. The stent may be formed as a single loop, as a plurality of loops extending in an axial direction, or as a helix. The flex cell may comprise a member in the shape of a U, V, a parallelogram, or a similar shape. Said flex cell has two ends, or in the case of the parallelogram two vertices, each of which is attached to the adjacent second end of a neighboring elongated member.

BRIEF DESCRIPTION OF THE DRAWINGS

A more complete appreciation of the subject matter of the present invention and the various advantages thereof can be realized by reference to the following detailed description, in which reference is made to the accompanying drawings in which.

DETAILED DESCRIPTION OF THE PREFERRED EMBODIMENTS

Figure 1:
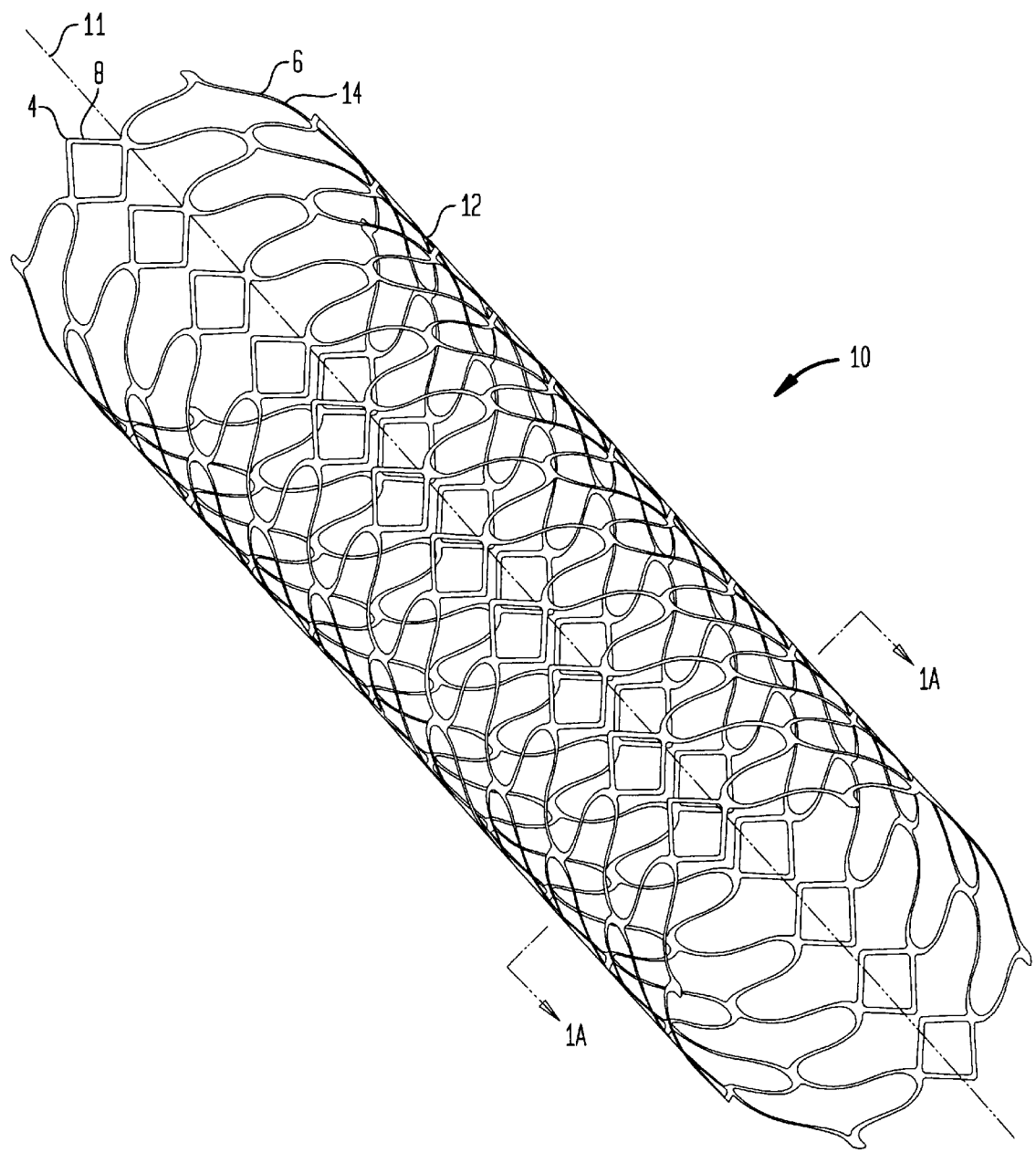
FIG. 1 is a perspective view of a flexible high radial strength stent in an expanded condition in accordance with one embodiment of the present invention.
Figure 1A:
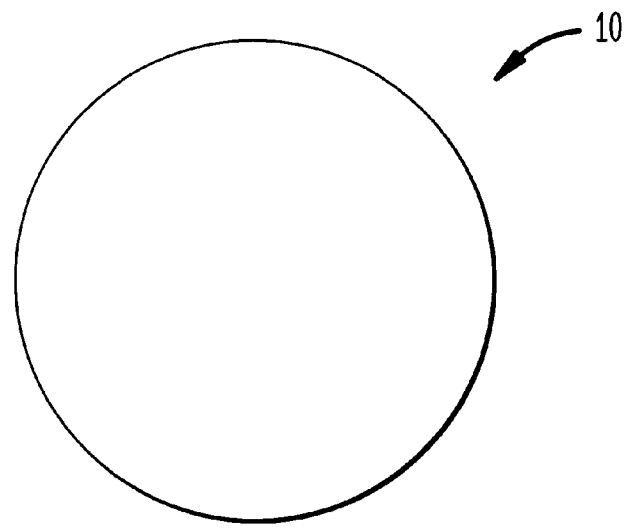
FIG. 1A is a transverse cross sectional view taken along lines 1A—1A in FIG. 1.

FIG. 1 is a perspective view of one embodiment of the stent of the present invention, generally designated 10. FIG. 1A illustrates a transverse cross sectional view of stent 10 taken along lines 1A—1A.

Stent 10 may be formed from a filament 12 of a low shape-memory material. As used herein, the term "low shape-memory material" refers to materials that, once deformed from an initial shape to a subsequent shape, will tend to maintain the subsequent shape and not return to the initial shape. In this regard, filament 12 is preferably formed from a biologically-compatible metal. Such metals may include, for example, stainless steel, titanium, tantalum, gold, platinum, copper and the like, as well as alloys of these metals. Biologically-compatible low shape-memory plastics may also be used to form filament 12. Alternatively, filament 12 may be formed from a shape-memory plastic or alloy, such as Nitinol, which may be designed to automatically transform from one shape to another shape as its temperature passes through a critical point.

Desirably, filament 12 comprises an elastic material; highly elastic materials being most preferred because of their tendency to return to their original shape following deformation. Whether filament 12 is formed from a low shape-memory material or from a shape-memory material is not critical, and impacts on the present invention predominantly in terms of the technique used to intraluminally deliver the stent to the repair site and fix same in place. In that regard, stents formed from low shape-memory materials are ordinarily delivered by a catheter to the repair site and expanded in a well-known manner by dilation of an angioplasty balloon, while stents formed from shape-memory alloys are normally thermally insulated in a catheter during delivery to the repair site and expand automatically upon passing through the critical temperature following deployment from the catheter.

Filament 12 may have a round cross-section as is typical of wires, or it may have a cross-section which is rectangular or another shape as desired. The size of the cross-section ordinarily will depend upon the particular application for which stent 10 is to be used. Moreover, the cross-section of the filament need not be constant along its entire length, but may include portions having a larger or smaller cross-section as desired. Filament 12 also need not be formed from a single continuous filament, but may consist of lengths of filament welded or otherwise joined together in end-to-end fashion.

Figure 2:
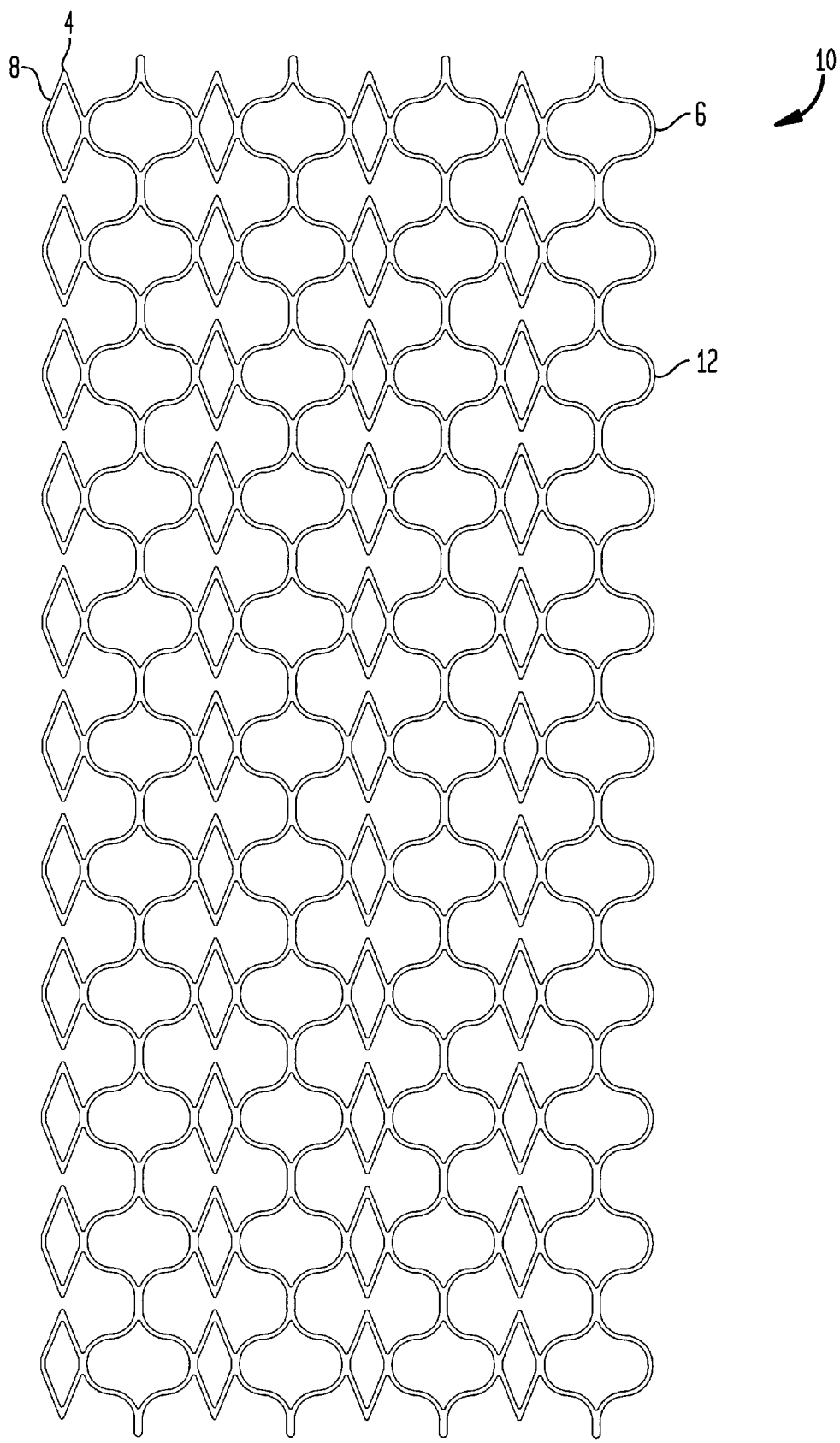
FIG. 2 is a plan view of the stent of FIG. 1 in an unrolled state.

Stent 10, as illustrated unrolled in FIG. 2, has eleven rows of cells, each row comprising four primary cells 6 and four flex cells 8. Flex cells 8 have a parallelogram shape and have four vertices 4. It should be noted that the number and distribution of primary cells 6 and the flex cells 8 will vary depending on the required geometry and physical properties required of the stent 10. The more flex cells 8 used in the stent 10, the more flexible the stent 10 becomes. It should further be noted that an ellipse or rhombus shape or other shapes similar to the parallelogram may be used for the flex cell 8.

Figure 3:
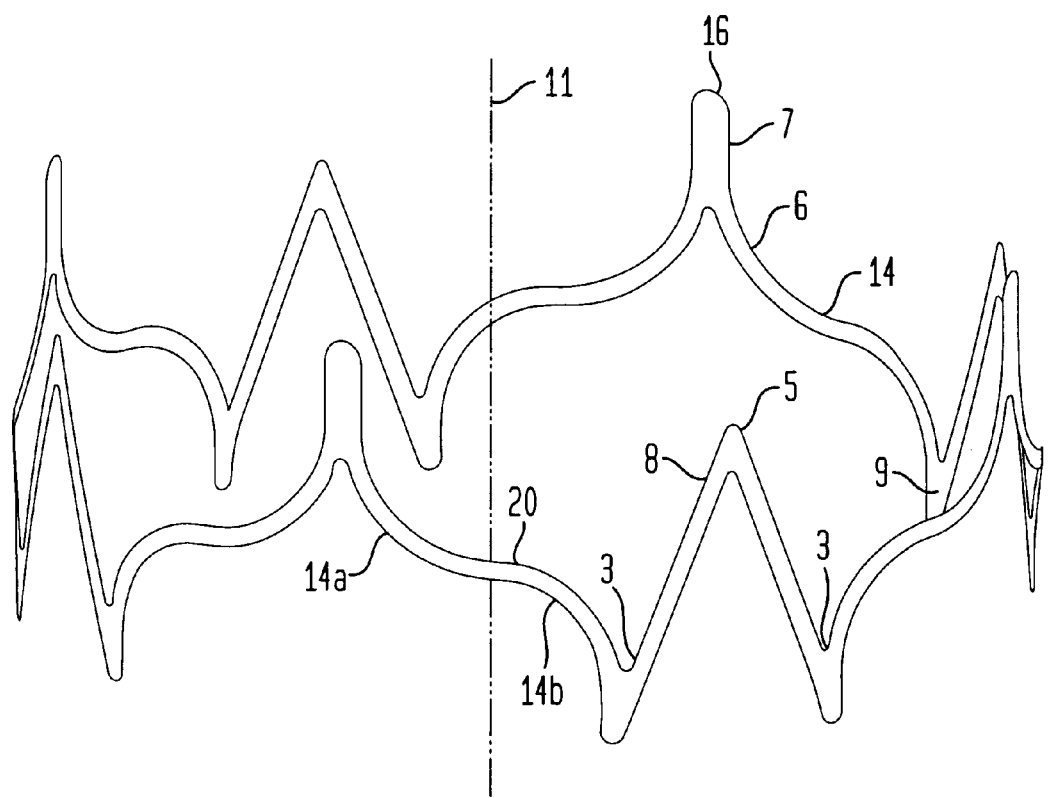
FIG. 3 is a perspective view of a row of half cells from the stent in FIG. 1.

For clarity purposes the structure of the stent 10 will be described by focusing on a row of rolled half cells, as illustrated in FIG. 3. V-shaped half flex cell 8 has two ends 3 and a V junction 5. Half primary cell 6 comprises smoothly curved elongated members 14 which extend in a circumferential direction about a central axis 11 of the stent 10. Elongated members 14 are joined to one another in an end-to-end relationship at their first ends 7 at sharply bent cusps 16 and at their second ends 9 to one end 3 of V-shaped half flex cell 8. The primary cells 6 and the flex cells 8 together define an enclosed loop. Stent 10 may consist of discrete portions of filament 12 which are welded or otherwise joined together at cusp 16 and at the V junction 5. Alternatively, stent 10 may be formed from a single continuous filament 12 bent into the configuration of elongated members 14 and cusp 16. The row of half cells can be combined in a variety of configurations with other rows of half cells to form a tubular stent. As illustrated in FIG. 1, ends 3 of each half flex cell 8 are connected to form rows of full cells.

Referring to FIGS. 1 and 3, each elongated member 14 is smoothly curved in opposite axial directions along substantially its entire length between cusp 16 and end 3 of the V shaped flex cell 8. That is, each elongated member 14 curves upwardly along a first portion 14a and downwardly along a second portion 14b, with the transition between the upwardly and downwardly curved portions occurring at a point of inflection 20. The first portion 14a defines a first arc and the second portion 14b defines a second arc. By curving elongated members 14 along substantially their entire length, substantially all of filament 12, used for the primary cells 6, contributes to the radial strength of stent 10. It is preferred that the first arc and second arc have a constant radius of curvature over an angle of between about 30 degrees and about 180 degrees. In this regard, the hoop strength of stent 10 in accordance with the present invention will be greater than the hoop strength of conventional stents regardless of the shape in which elongated members 14 are curved. The flexibility of the primary cells 6 can be controlled by varying the angle of the first and second arcs. The higher the angle the stiffer the primary cell 6, and accordingly, the stiffer the stent 10.

Figure 4:
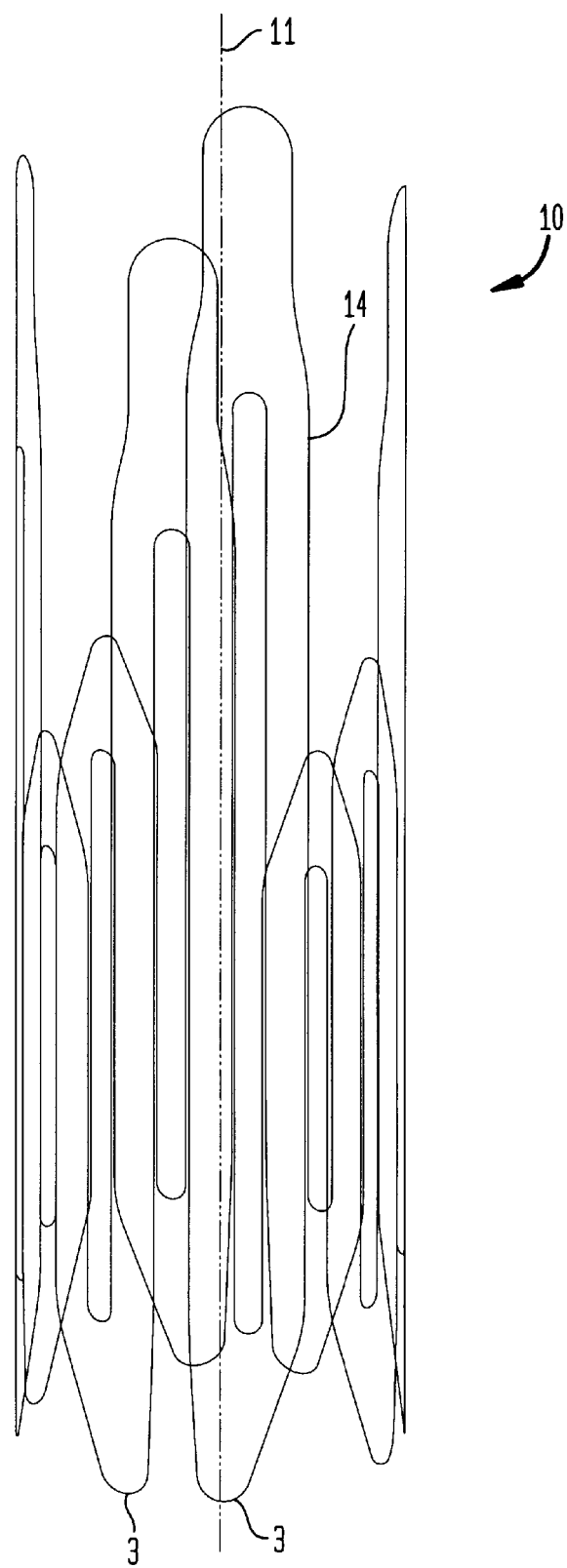
FIG. 4 is a perspective view of the row of half cells of FIG. 3 in an axially compressed state.

FIG. 4 illustrates a perspective view of stent 10 radially compressed. Upon compression, elongated members 14 straighten and ends 3 of V shaped flex cell 8 (FIG. 3) approach each other.

Figure 5:
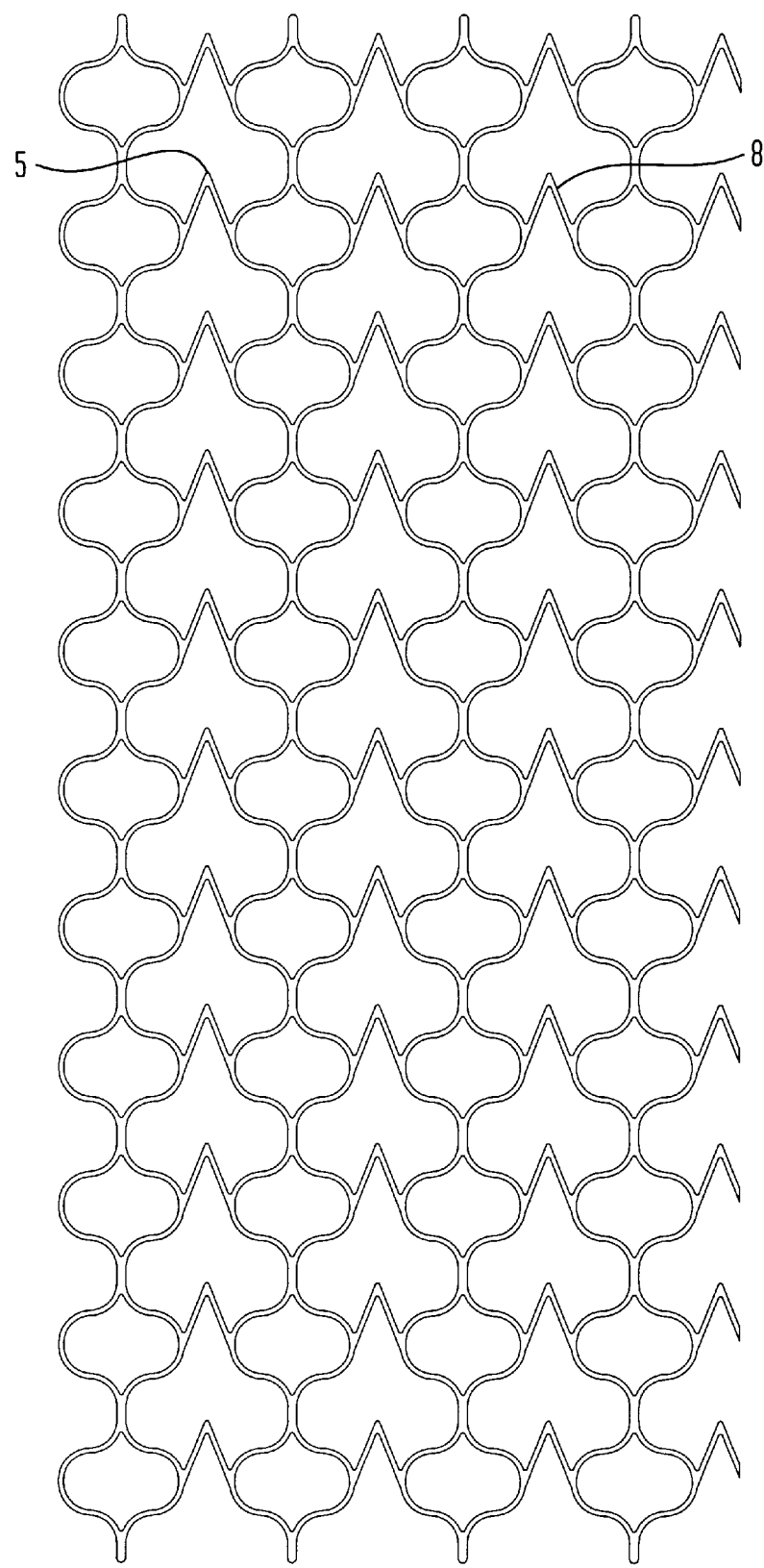
FIG. 5 is a plan view of another embodiment of the stent of the present invention in an unrolled state.

In an alternative embodiment of the invention, as illustrated in FIG. 5, the full flex cell comprises a V shaped member 8. As illustrated, all the V shaped members 8 have their V junctions 5 pointing in the same direction, however, some or all of V junctions 5 may be oriented in the opposing axial direction as well. Note that the V shaped members 8 may be replaced with similarly shaped members, such as but not limited to, U shaped members.

In another alternative embodiment of the invention the entire stent 10 may comprise only primary cells 6. The primary cells 6 may be specifically designed to provide the required flexibility required of the stent 10 or a particular area of the stent 10. As discussed above, reducing the angle of the arc defined by the elongated members 14 in a specific primary cell 6 reduces the stiffness and increases the flexibility of the primary cell 6. Thus, the entire stent 10 can be made more flexible by using smaller arc angles. Similarly, specific regions of the stent 10 can be made more flexible by lowering the arc angle in primary cells 6 in the area in which increased flexibility is desired.

In the embodiments discussed above, the circumference of each circumferential loop or convolution of the illustrated stent 10 is substantially the same. It will be appreciated, however, that this need not be the case and that the circumference of adjacent loops or convolutions can differ so as to form an elongated stent having a shape that is different from that of a right cylinder. For example, by altering the circumference of adjacent sections, stents having tapered or stepped profiles can be provided.

Although the invention herein has been described with reference to particular embodiments, it is to be understood that these embodiments are merely illustrative of the principles and applications of the present invention. It is therefore to be understood that numerous modifications may be made to the illustrative embodiments and that other arrangements may be devised without departing from the spirit and scope of the present invention as defined by the appended claims.

What is claimed is:

1. A stent in an uncompressed state comprising one or more substantially V-shaped axially oriented members extending in a circumferential direction around an axis and a plurality of elongated members having a first end and a second end and extending in a circumferential direction around said axis and curving in two opposite directions transverse to said circumferential direction, the first end of each said elongated member joining the first end of another elongated member to define a cusp pointing in a direction transverse to said circumferential direction, each said cusp including a portion of one elongated member curving in a direction away from a portion of an adjacent elongated member.

2. The stent as claimed in claim 1 wherein each said elongated member has a constant radius of curvature between said cusps.

3. The stent as claimed in claim 1 wherein one or more of the substantially V-shaped members and said plurality of elongated members define a loop which is foldable between a collapsed circumference and an expanded circumference greater than said collapsed circumference.

4. The stent as claimed in claim 3 wherein the V-shaped member has a two ends each of which is connected to the second end of an adjacent elongated member.

5. The stent as claimed in claim 3 wherein each said elongated member includes a first portion curving in a first direction and a second portion curving in a second direction opposite to the first direction.

6. The stent as claimed in claim 5 wherein each said first portion of said members define an arc having a constant radius of curvature over an angle of between about 30 degrees and about 180 degrees.

7. The stent as claimed in claim 5 wherein each said second portion of said members define an arc having a constant radius of curvature over an angle of between about 30 degrees and about 180 degrees.

8. A stent an uncompressed state consisting of plurality of axially orientedflex cells and a plurality of primary cells, said primary cells comprising elongated members having a first end and a second end and extending in a circumferential direction around an axis and curving in two opposite directions transverse to said circumferential direction, the first end of each said elongated members joining the first end of another elongated member to define a cusp pointing in directions transverse to said circumferential direction, each said cusp including a portion of one elongated member curving in a direction away from a portion of an adjacent elongated member, each said elongated member includes a first portion curving in a first direction and a second portion curving in a second direction opposite to the first direction, the first portion defines a first arc and the second portion defines a second arc, said primary cells forming a loop, said stent comprising one or more loops, at least one of said loops having at least one flex cell, said flex cell being more flexible than said primary cells.

9. The stent as claimed in claim 8 wherein the flex cells comprise elongated members extending in a circumferential direction around an axis and curving in two opposite directions transverse to said circumferential direction, said elongated members joining one another on one end to define cusps pointing in directions transverse to said circumferential direction, each said cusp including a portion of one elongated member curving in a direction away from a portion of an adjacent elongated member, each said elongated member includes a first portion curving in a first direction and a second portion curving in a second direction opposite to the first direction, the first portion defines a first arc and the second portion defines a second arc, the angle described by the first arc of the elongated member of the flex cell is lower than the angle described by the first arc of the elongated member of the primary cell.

10. The stent as claimed in claim 8 wherein the flex cell has a V shape.

11. The stent as claimed in claim 10 wherein the flex cell has a two ends each of which is connected to the second end of an adjacent elongated member.

12. The stent as claimed in claim 8 wherein the flex cell is a parallelogram having four vertices, one vertex is connected to the second end of an elongated member, an opposing vertex is connected to the second end of an adjacent elongated member.

13. The stent as claimed in claim 8 wherein the flex cell is a rhombus having four vertices, one vertex is connected to the second end of an elongated member, the opposing vertex is connected to the second end of an adjacent elongated member.

14. The stent as claimed in claim 8 wherein the flex cells comprise elongated members extending in a circumferential direction around an axis and curving in two opposite directions transverse to said circumferential direction, each said elongated member being curved over substantially its entire extent, said elongated members joining one another on one end to define cusps pointing in directions transverse to said circumferential direction each said cusp including a portion of one elongated member curving in a direction away from a portion of an adjacent elongated member, each said elongated member includes a first portion curving in a first direction and a second portion curving in a second direction opposite to the first direction, the first portion defines a first arc and the second portion defines a second arc, the angle described by the second arc of the elongated member of the flex cell is lower than the angle described by the second arc of the elongated member of the primary cell.

15. The stent as claimed in claims 1 or 8 wherein each elongated member is curved substantially along its entire length.

* * * * *